(12) United States Patent
Winkler et al.

(10) Patent No.: US 12,023,157 B2
(45) Date of Patent: *Jul. 2, 2024

(54) DEVICE FOR CROSS FLOW FILTRATION

(71) Applicant: MANN+HUMMEL GmbH, Ludwigsburg (DE)

(72) Inventors: Dagmar Winkler, Filderstadt (DE); Heike Rupp, Kirchheim am Neckar (DE); Steffen Schuetz, Bietigheim-Bissingen (DE); Dietmar Talmon-Gros, Oberstenfeld (DE); Michael Fasold, Auenwald (DE); Alfons-Alois Schwinghammer, Dingolfing (DE); Frank Bartel, Ludwigsburg (DE); Sascha Bauer, Auenwald (DE); Patrick Nytz, Kirchenheim (DE)

(73) Assignee: MANN+HUMMEL GmbH, Ludwigsburg (DE)

( * ) Notice: Subject to any disclaimer, the term of this patent is extended or adjusted under 35 U.S.C. 154(b) by 349 days.

This patent is subject to a terminal disclaimer.

(21) Appl. No.: 16/891,394

(22) Filed: Jun. 3, 2020

(65) Prior Publication Data

US 2020/0289041 A1    Sep. 17, 2020

Related U.S. Application Data

(60) Division of application No. 14/983,192, filed on Dec. 29, 2015, now Pat. No. 10,687,750, which is a (Continued)

(30) Foreign Application Priority Data

Jul. 31, 2013 (DE) .................... 10 2013 012 676.2

(51) Int. Cl.
*A61B 5/15* (2006.01)
*A61B 5/153* (2006.01)
(Continued)

(52) U.S. Cl.
CPC .... *A61B 5/150755* (2013.01); *A61B 5/15003* (2013.01); *A61B 5/150229* (2013.01); (Continued)

(58) Field of Classification Search
CPC ........ A61B 5/150755; A61B 5/150244; A61B 5/15003; A61B 5/150503; (Continued)

(56) References Cited

U.S. PATENT DOCUMENTS 3,705,100 A * 12/1972 Rigopulos et al. . A61M 1/3603
604/6.04
4,744,955 A * 5/1988 Shapiro ................. B01L 3/0224
73/864.18

(Continued)

*Primary Examiner* — Jason M Greene
*Assistant Examiner* — Eric J McCullough

(57) ABSTRACT

A whole blood filtration device is provided with a filter membrane separating a feeding volume and a clean side of the filter membrane from each other. The feeding volume communicates with a first feeding side opening and with a second feeding side opening. The filter membrane has pores with a pore size that ensures permeability of the filter membrane to blood plasma/serum and that retains blood cells. The first feeding side opening can be coupled to a first blood pump for feeding blood from the first feeding side opening into the feeding volume so that blood plasma/serum permeates the filter membrane and blood cells, retained by the filter membrane, exit from the feeding volume through the second feeding side opening.

12 Claims, 5 Drawing Sheets

Related U.S. Application Data continuation of application No. PCT/EP2014/066485, filed on Jul. 31, 2014.

(51) Int. Cl.

| | |
|---|---|
| *A61M 1/02* | (2006.01) |
| *A61M 1/34* | (2006.01) |
| *A61M 1/36* | (2006.01) |
| *B01D 39/20* | (2006.01) |
| *B01D 63/02* | (2006.01) |
| *B01D 65/00* | (2006.01) |
| *B01D 67/00* | (2006.01) |
| *B01L 3/00* | (2006.01) |
| *G01N 1/40* | (2006.01) |
| *G01N 33/49* | (2006.01) |

(52) U.S. Cl.
CPC .. *A61B 5/150236* (2013.01); *A61B 5/150251* (2013.01); *A61M 1/34* (2013.01); *A61M 1/3496* (2013.01); *A61M 1/36* (2013.01); *A61M 1/3633* (2013.01); *B01D 63/0233* (2022.08); *B01D 63/028* (2013.01); *B01D 63/031* (2022.08); *B01D 65/00* (2013.01); *B01D 67/0088* (2013.01); *G01N 1/4005* (2013.01); *G01N 33/491* (2013.01); *A61B 5/150244* (2013.01); *A61B 5/150389* (2013.01); *A61B 5/150503* (2013.01); *A61B 5/153* (2013.01); *A61M 1/0281* (2013.01); *A61M 2205/3331* (2013.01); *B01D 39/2068* (2013.01); *B01D 2311/02* (2013.01); *B01D 2313/10* (2013.01); *B01D 2313/12* (2013.01); *B01D 2313/24* (2013.01); *B01D 2313/901* (2022.08); *B01D 2323/04* (2013.01); *B01D 2323/20* (2013.01); *B01L 3/502* (2013.01); *B01L 2300/0681* (2013.01); *B01L 2400/0478* (2013.01); *B01L 2400/0481* (2013.01); *G01N 2001/4016* (2013.01); *G01N 2201/0221* (2013.01); *G01N 2201/0222* (2013.01); *G01N 2800/22* (2013.01)

(58) Field of Classification Search
CPC ........ A61B 5/150236; A61B 5/150251; A61B 5/150389; A61B 5/153; A61B 5/150229; A61M 1/36; A61M 1/3496; A61M 1/3633; A61M 1/34; A61M 1/0281; A61M 2205/3331; G01N 33/491; G01N 1/4005; G01N 2001/4016; G01N 2201/0221; G01N 2201/0222; G01N 2800/22; B01D 63/021; B01D 63/02; B01D 67/0088; B01D 65/00; B01D 63/028; B01D 2323/04; B01D 2313/90; B01D 2311/02; B01D 2313/10; B01D 2313/24; B01D 2323/20; B01D 2313/12; B01D 71/02; B01D 63/029; B01D 71/024; B01D 39/2068; B01L 3/502; B01L 2400/0478; B01L 2400/0481; B01L 2300/0681

See application file for complete search history.

(56) References Cited

U.S. PATENT DOCUMENTS

| | | | | |
|---|---|---|---|---|
| 4,789,473 | A * | 12/1988 | Mathieu | B29C 70/845 210/321.89 |
| 4,888,109 | A * | 12/1989 | Manohar | B01D 63/02 210/321.62 |
| 4,966,699 | A * | 10/1990 | Sasaki | B01D 69/08 210/450 |
| 5,674,394 | A * | 10/1997 | Whitmore | A61M 1/3496 422/534 |
| 2008/0035568 | A1 * | 2/2008 | Huang | B01D 71/024 210/645 |
| 2008/0058695 | A1 * | 3/2008 | Perovitch | A61M 1/02 604/6.03 |

* cited by examiner

DEVICE FOR CROSS FLOW FILTRATION

CROSS-REFERENCE TO RELATED APPLICATIONS

This application is a Divisional application of US application Ser. No. 14/983,192 having a US filing date of 29 Dec. 2015, which is a Continuation of international application No. PCT/EP2014/066485 having an international filing date of 31 Jul. 2014 and designating the United States, the international application claiming a priority date of 31 Jul. 2013, based on prior filed German patent application No. 10 2013 012 676.2, the entire contents of the aforesaid US application, the aforesaid international application and the aforesaid German patent application being incorporated herein by reference to the fullest extent permitted by the law.

BACKGROUND OF THE INVENTION

The present invention relates to a device for cross flow filtration, and in particular to a whole blood filtration device allowing a fast and simple filtering process for separation of blood cells.

Separation of blood cells is required in particular for purposes of analysis of the human blood. A separation can be obtained by centrifugation of the human blood to thereby obtain the separated plasma/serum and blood cells. However, a centrifugation process requires an extraordinary apparatus and also requires a certain period of time. In particular, in emergency applications, for example, in ambulances, a centrifugation process is not practicable. Further, for private use or for pharmacies, a centrifugation process is expensive and of extraordinary effort. Therefore, there is a need for a simple and low-cost device for whole blood filtration.

A subsequent whole blood separation into plasma/serum can be advantageous for point-of-care testing devices, which are used to provide a quick blood analysis at/near the patient to get a quick blood analysis result outside of a clinical laboratory to make immediate decisions about patient care. Typically point-of-care testing is performed by non-laboratory personnel. A quick prior plasma filtration process facilitates the quick blood analysis and enables new operating conditions for point-of-care devices, since most of them work with whole blood or with the aforementioned microdevices which lead to a very small yield of plasma/serum volume. The whole blood separation process can also be integrated within the point-of-care device.

SUMMARY OF THE INVENTION

The present invention provides a whole blood filtration device that comprises a simple configuration, is reliable, and enables a fast filtration process.

As used herein, the term "whole blood" refers to blood composed of blood plasma, which is typically unclotted, and cellular components. The plasma represents about 50% to about 60% of the volume, and cellular components, i.e. erythrocytes (red blood cells, or RBCs), leucocytes (white blood cells, or WBCs), and thrombocytes (platelets), represent about 40% to about 50% of the volume. As used herein, the term "whole blood" may refer to whole blood of an animal, but preferably to whole blood of a human subject.

Erythrocytes constitute about 90% to about 99% of the total number of all blood cells and have the form of biconcave discs; they measure about 7 μm in diameter with a thickness of about 2 μm in an undeformed state. During maturation in the bone marrow the erythrocytes lose their nucleus. They contain the plasma membrane protein spectrin and other proteins to provide flexibility to change shape as necessary. Their unique and flexible shape enables them to pass through very narrow capillaries and provides for maximum surface area to transfer oxygen and carbon dioxide. This flexibility makes it particularly difficult to separate the red blood cells from a whole blood sample by filtration as they can elongate themselves and reduce their diameter down to about 1.5 μm. Normal whole blood has approximately 4.5 million to 5.5 million erythrocytes per microliter. The life-span of erythrocytes is approximately 120 days in the circulating bloodstream. One core component of erythrocytes is hemoglobin which binds oxygen for transport to the tissues, then releases oxygen and binds carbon dioxide to be delivered to the lungs as waste product. Hemoglobin is responsible for the red color of the erythrocytes and therefore of the blood in total. Erythrocytes are the major factor contributing to blood viscosity.

Leucocytes make up less than about 1% of the total number of all blood cells and can be differentiated into different white blood cell groups (lymphocytes, granulocytes, and monocytes). They can leave capillaries via diapedesis. Furthermore, they can move through tissue spaces by amoeboid motion and positive chemotaxis. They have a diameter of about 6 μm to about 20 μm. Leucocytes participate in the body's defense mechanisms e.g. against bacterial or viral invasion.

Thrombocytes are the smallest blood cells with a length of about 2 μm to about 4 μm and a thickness of about 0.9 μm to about 1.3 μm. They are membrane-bound cell fragments that contain enzymes and other substances important to clotting. In particular, they form a temporary platelet plug that helps to seal breaks in blood vessels.

The terms "blood plasma" or "plasma" refer to the liquid part of the blood and lymphatic fluid, which makes up about half of the volume of blood (e.g. about 50 vol.-% to about 60 vol.-%). Plasma is devoid of cells, and unlike serum, has not clotted. So it contains all coagulation factors, in particular fibrinogen. It is a clear yellowish liquid including about 90 vol.-% to about 95 vol.-% water.

The term "blood serum" or "serum" refers to the clear liquid that separates from blood when it is allowed to clot completely, and is therefore blood plasma from which in particular fibrinogen has been removed during clotting. Like plasma, serum is light yellow in color.

As used herein, the term "cell-free" describes a plasma/serum sample with no or substantially no cells (erythrocytes, leucocytes, thrombocytes) in its volume that is prepared by e.g. a centrifuge. A substantially cell-free sample or a cell-free sample is needed for a subsequent plasma/serum analysis to prevent blocking of the analysis system.

As used herein, the term "clean side" describes the cell-free side of the filter. The separated blood plasma/serum may be collected on the clean side of the filter.

As used herein, the term "hemolysis" refers to the rupture of erythrocytes, e.g. due to chemical, thermal or mechanical influences, causing the release of the hemoglobin and other internal components into the surrounding fluid. Hemolysis can be visually detected by showing a pink to red tinge in the plasma/serum.

The term "hydrophilic" refers to a surface, which leads to a water or blood droplet contact angle smaller than 90°, "hydrophobic" surfaces lead to a water or blood droplet contact angle bigger than 90°.

The term "reduced hydrophilicity" refers to a water or blood droplet contact angle bigger than the water or blood droplet contact angle of an untreated hollow fiber membrane filter medium.

The MWCO is defined as the molecular weight solute (in Daltons, Da) in which 90%, preferably 95%, more preferably 99% of the solute is retained by the membrane, or the molecular weight of the molecule (e.g. globular protein) that is 90%, preferably 95%, more preferably 99% retained by the membrane.

In a preferred embodiment, the whole blood hollow fiber membrane filter medium allows molecules of less than about 8,000 kDa, preferably less than about 10,000 kDa, more preferably less than about 20,000 kDa, to pass. In other words, the molecular weight cut-off (MWCO) is above 8,000 kDa, preferably above 10,000 kDa, more preferably above 20,000 kDa. As a consequence, erythrocytes, leukocytes, and thrombocytes are retained, but blood plasma components are not retained.

According to an exemplary embodiment of the invention, there is provided a whole blood filtration device including a feeding volume having a first feeding side opening and a second feeding side opening, a clean side, and a filter membrane, wherein the filter membrane separates the feeding volume and the clean side, wherein the filter membrane has pores of a pore size ensuring permeability to blood plasma/serum, but retaining blood cells, wherein the first feeding side opening is adapted to be coupled to a first blood pump, preferably by a Luer lock connection, for feeding blood from the first feeding side opening into the feeding volume so that blood plasma/serum may permeate the filter membrane and blood cells may exit the feeding volume through the second feeding side opening.

Thus, it is possible to provide a simple device for blood filtration so that plasma/serum can quickly be separated from the human blood for analysis purposes. For analysis purposes, either the obtained plasma/serum or the cell concentrate can be used. The above-described device has a simple configuration and is easy to handle so that it is also useful outside of labs and in cases where no centrifugation apparatus is available. The membrane is adapted to allow blood plasma/serum to pass and to retain blood cells. In particular, the membrane may be adapted to allow a certain amount of plasma/serum per flow-through cycle to pass so that an amount of plasma/serum is accumulated when running a plurality of flow through iterations. The filter area of the membrane, i.e. the surface facing a raw side of a filter medium, e.g. a lumen of a hollow fiber membrane filter medium, or feeding volume of the filter may be adapted to avoid adhesion and mechanical/chemical destruction of blood cells, so that the fluid of blood cells and remaining plasma/serum may wash away blood cells so that clogging of the membrane may be avoided.

According to an exemplary embodiment of the invention, the second feeding side opening is adapted to be coupled to a second blood pump, preferably by a Luer lock connection, for feeding blood from the second feeding side opening to the feeding volume so that a blood plasma/serum may permeate the filter membrane and blood cells may exit the volume through the first feeding side opening.

Thus, it is possible to generate a forward and backward blood flow through the whole blood filtration device so that, in each iteration, a certain amount of plasma/serum may be separated from the whole blood. In particular, the blood flow may be generated forward and backward iteratively, until the desired amount of plasma/serum has been separated from the whole blood. It should be noted that a blood pump may be a motor-driven device, a manually driven device, or just a device in combination with an energy storing element, like a spring or a compressible air volume or the like, so that an automatic return flow is generated.

According to an exemplary embodiment of the invention, a whole blood filtration device further comprises at least one blood pump being coupled to one of the first feeding side opening and second feeding side opening.

Thus, it is possible to have a complete whole blood filtration device on hand, including the blood pump, so that the filtration process can directly be started. It should be noted that the blood pump may be removed for filling the blood pump with blood. The blood pump may be exchanged.

According to an exemplary embodiment of the invention, the at least one blood pump is actuated automatically e.g. electrically or pneumatically or magnetically driven.

According to an exemplary embodiment of the invention, the at least one blood pump is a manual blood pump.

Thus, a whole blood filtering device may be provided which does not require a power source. The blood pump may be a syringe having a coupling portion for coupling a needle.

According to an exemplary embodiment of the invention, the whole blood filtration device further comprises a second blood pump being coupled to one of the first feeding side opening and the second feeding side opening.

Thus, no further motor-driven elements are required and the whole blood filtration device may be used independent of energy. In particular, the manual blood pump may be a syringe which also may be used for taking blood from a human vein. In particular, the needle may be removed from the syringe, and the syringe may be plugged to the whole blood filtration device. For this purpose, one of the first feeding side opening and the second feeding side opening may be open and not coupled to a blood pump, wherein the other of the first feeding side opening and the second feeding side opening may be coupled with the second blood pump for receiving the remaining whole blood at the other side of the first feeding side opening and the second feeding side opening.

According to an exemplary embodiment of the invention, the second blood pump comprises a resilient volume being adapted for being biased by a biasing force upon reception of a blood fluid and for releasing blood fluid when the biasing force is reduced.

Thus, the second blood pump may receive the remaining blood not yet finally filtered and store the blood so that the blood may flow back for the next iteration of the filtering process. Thus, it is possible to only actuate one blood pump, wherein the other blood pump owing to the resilient volume expands for receiving the blood fluid and contracts for releasing the blood fluid. For example, as the second blood pump, a resilient rubber or a spring-loaded plunger may be used so that, at the first blood pump side, a pressure may be applied for a forward flow, and when releasing the pressure, a resilient property of the second blood pump will induce return flow of the fluid back to the first blood pump; the forward and backward flow process may be repeated with actuation of only the first blood pump side. The biasing member may be an air volume in a cylinder. The receiving volume of the cylinder may be separated by a movable plunger from the biasing air volume.

According to an exemplary embodiment of the invention, the filter membrane comprises at least one hollow fiber membrane filter medium having a lumen with a first end-side (terminal) opening and a second end-side (terminal) opening, wherein the lumen comprises the feeding volume so that the first feeding side opening is in communication with the first end-side opening and the second feeding side opening is in communication with the second end-side opening.

Thus, the filtering process may be conducted by a cross-flow filtration by way of the hollow fiber membrane filter medium. In particular, a plurality of hollow fiber membranes may be applied also, wherein the plurality of lumen of the plurality of hollow fiber membranes each have a first end-side opening and a second end-side opening, and the plurality of first end-side openings are in communication with the first feeding side opening, and the plurality of second end-side openings are in communication with the second feeding side opening. In particular, the hollow fiber membranes may be potted within the filter housing at the side of the first end-side opening and the side of the second end-side opening so as to have a fluid-tight connection to the first and second feeding side openings. The hollow fiber membranes may be ceramic hollow fiber membranes or polymer hollow fiber membranes.

According to an exemplary embodiment of the invention, the whole blood filtration device further comprises a filter housing which filter housing contains the filter membrane, wherein the filter housing comprises the first feeding side opening and the second feeding side opening, wherein the filter housing further comprises an outlet opening in communication with the clean side.

Thus, the separated blood plasma/serum may be collected on the clean side and may be collectively fed to an outlet opening, which outlet opening may be, for example, coupled to a further container, like a syringe. The outlet opening may also be coupled to a plasma/serum collector which subsequently may be subjected to an analysis procedure. The filter housing may taper toward the outlet to support the filtrate drainage. The filter housing may be a two-part filter housing having receiving portions for receiving the hollow fiber membrane or hollow fiber membrane bundle. The receiving portions may tightly clamp the hollow fiber membrane or fiber membrane bundle. This simplifies the manufacturing process, as the hollow fiber membrane or fiber membrane bundle may be clamped at the end sides of both filter housing portions when assembling the filter housing.

According to an exemplary embodiment of the invention, the hollow fiber membrane is a fiber pre-treated by an ionic solution.

The pre-treatment of a hollow fiber membrane by an ionic solution may reduce hemolysis, which hemolysis means the destruction of the blood cells, in particular the red blood cells. The ionic solution may be for example a sodium chloride (NaCl) solution, in particular an isotonic NaCl solution (0.9% m:v), which may result in a reduction of the osmotic pressure within the blood cells and in a prewetting of the hollow fiber membrane to reduce capillary effects.

According to an exemplary embodiment of the invention, the hollow fiber membrane is made of a ceramic material having a pore size ensuring permeability to blood plasma/serum, but retaining blood cells.

According to an exemplary embodiment of the invention, the hollow fiber membrane is a membrane being coated to reduce hydrophilicity. Hydrophilicity should be reduced preferably at the filter area where the whole blood first contacts the membrane. Due to reduced hydrophilicity, the capillary effects become less destructive for the blood cells.

Thus, it is possible to provide an inert and hemocompatible material for the hollow fiber membrane which material allows a proper filtering process to separate blood plasma/serum from the remaining blood cells.

According to an exemplary embodiment of the invention, the hollow fiber membrane is made of a polymeric material having a pore size ensuring permeability to blood plasma/serum, but retaining blood cells.

Thus, it is possible to have a hollow fiber membrane of a material which is easy to manufacture.

According to an exemplary embodiment of the invention, the filter housing has a longitudinal extension, the first feeding side opening has a first opening orientation and the second feeding side opening has a second opening orientation, wherein the first opening orientation and the second opening orientation each can be inclined to the longitudinal extension of the filter housing, wherein the inclination between the longitudinal extension of the filter housing and the first opening orientation and the inclination between the longitudinal extension of the filter housing and the second opening orientation is between 10° and 80°, preferably between 30° and 60°, and more preferably 45°+/−5°.

Thus a blood pump to be coupled to the first feeding side opening and the second feeding side opening is easier to handle. The device allows an anatomically correct handling. According to an exemplary embodiment, the outlet opening is oriented away from the first and second opening orientation.

According to an exemplary embodiment of the invention, the whole blood filtration device further comprises a first resilient balloon as a blood pump fixedly connected to the first feeding side opening and further comprises a second resilient balloon as a blood pump fixedly connected to the second feeding side opening, wherein the filter housing further comprises a sample inlet opening in communication with the filter volume to feed the blood sample.

Thus, handling is easier as no piston has to be moved. The filtration device including the blood pumps may be designed as a closed system with only a single inlet opening and a single outlet opening. The inlet opening and the outlet opening are well defined so that the entire device can be easily kept aseptic.

According to an exemplary embodiment of the invention, the sample inlet opening is designed as a cannula needle in communication with the filter volume for feeding the blood sample.

Thus, a blood sample may be easily plugged in, in particular a standard blood container as sample container having a perforable septum.

According to an exemplary embodiment of the invention, the filter housing has a U-shaped configuration and the first feeding side opening and the second feeding side opening have a corresponding opening orientation so that a first blood pump and a second blood pump to be connected may be arranged side by side.

Thus, the device may be designed in a compact way and may be easy to handle. In particular, both blood pumps may have push buttons arranged side by side.

According to an exemplary embodiment of the invention, the whole blood filtration device further comprises a first blood pump removably connected to the first feeding side opening and a second blood pump removably connected to the second feeding side opening, wherein the first blood pump and the second blood pump are arranged side by side and form together a single unit.

Thus, a modular system can be provided with corresponding plugs. The pump unit with two pumps has two openings having a geometry corresponding to the feeding opening arrangement including the first and second feeding openings of the filter housing so that both pumps may be connected to the filter housing by a single plug-in step. This may be of high relevance in emergency medicine applications or point-of-care testing devices.

According to an exemplary embodiment of the invention, the first blood pump and the second blood pump are piston-driven manual blood pumps, each having a push button, wherein the push buttons have a corresponding operating orientation.

Thus, the push buttons may alternately be operated when the whole blood filtration device is handheld. For example, the push buttons may alternately be operated by a user's thumb when the device is handheld.

According to an exemplary embodiment of the invention, one of the first blood pump and the second blood pump when being de-coupled from the filter housing can be removably coupled to a cannula needle to take blood from a patient.

Thus, the blood pump can directly be used for taking blood from a patient without the need for transfer of the blood into the pump.

According to an exemplary embodiment of the invention, the filter housing is tapered toward the outlet opening.

Thus, the plasma/serum arrives gravity-driven at the outlet opening, correct orientation presumed.

According to an exemplary embodiment of the invention, the filter housing surface at the clean side is hydrophobic or hydrophobically coated.

Thus, a waste of plasma/serum by adhesion to the filter housing may be avoided.

It should be noted that the above features may also be combined. The combination of the above features may also lead to synergetic effects, even if not explicitly described in detail.

In another embodiment of the process, the sample of whole blood is depleted of blood cells by a different method, after which there are still blood cells present in the sample, e.g. by incomplete separation of the blood cells from serum/plasma by centrifugation or by sedimentation.

The whole blood filtration device according to the present invention may also be used as a solid-liquid or liquid-liquid separation tool in other fields, e.g. in veterinary medicine, food technology, environmental sciences, and in scientific laboratories in general. In particular, the whole blood filtration device can be used in efficient and mild separation methods of highly concentrated suspensions, cellular systems and sensitive particulate systems. It is highly preferred to use the whole blood filtration device according to the present invention in filtration processes, wherein the volume of the sample to be separated and the volume of the filtrate is small, e.g. less than 20 ml, preferably less than 10 ml, which is e.g. the case in the analytical quality assurance in production processes.

These and other aspects of the invention will become apparent from and be elucidated with reference to the embodiments described hereinafter.

BRIEF DESCRIPTION OF THE DRAWINGS

Exemplary embodiments of the present invention will be described in the following with reference to the following drawings.

DESCRIPTION OF THE INVENTION

Figure 1:
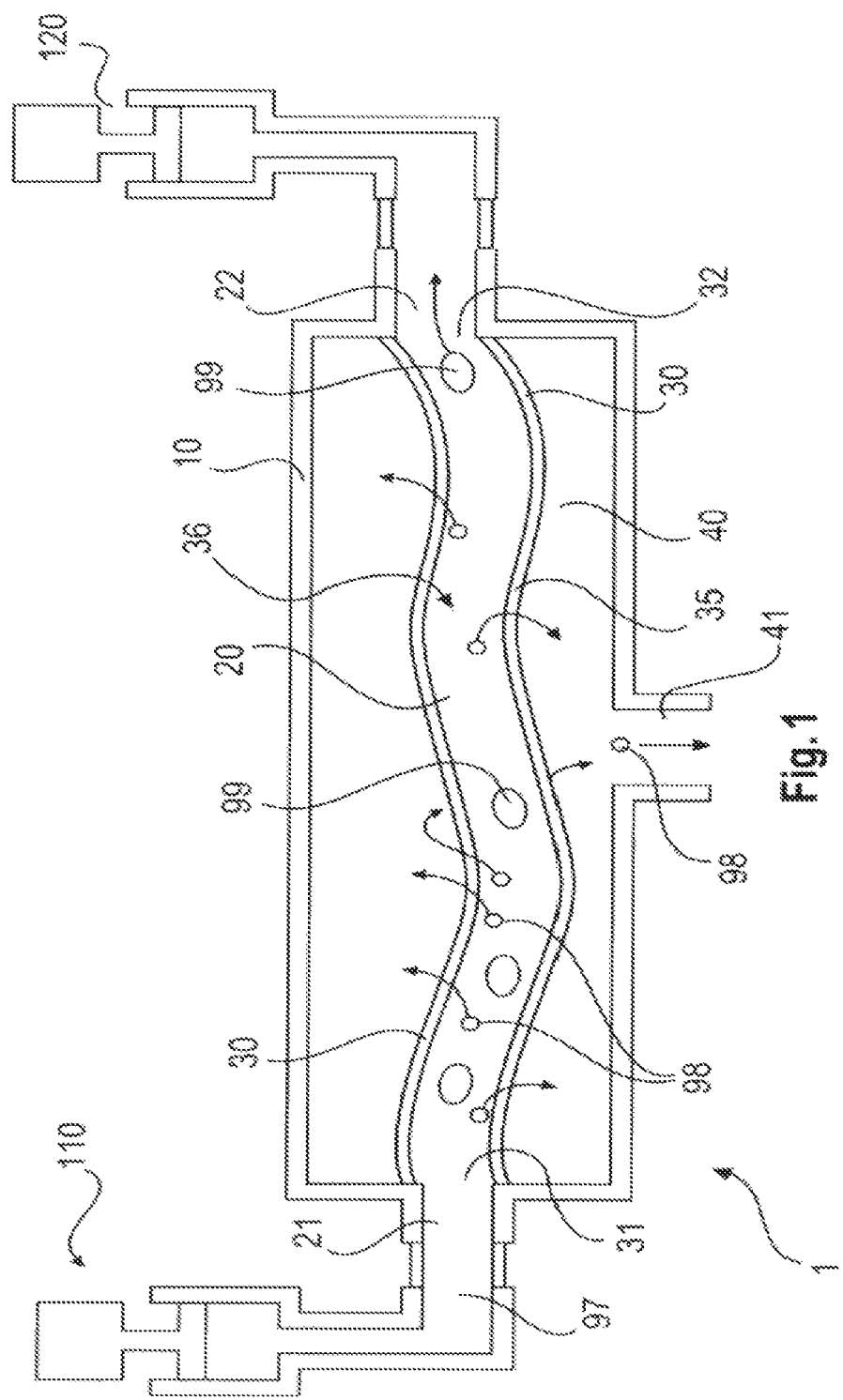
FIG. 1 illustrates an exemplary whole blood filtration device according to the invention.

FIG. 1 illustrates an exemplary embodiment of a whole blood filtration device. The whole blood filtration device 1 comprises a filter housing 10. The filter housing 10 may house the filter membrane 30, which filter membrane 30 may be in the shape of a hollow fiber membrane 35. FIG. 1 exemplarily illustrates one hollow fiber membrane, in particular in an enlarged view. However, it is understood that also a plurality of hollow fiber membranes may be used within the filter housing 10.

The filtration device comprises a feeding volume 20, which feeding volume receives the whole blood to be filtered. The filter membrane 30 separates the feeding volume, i.e. the raw side of the filter medium, from the clean side. When providing a filtration device 1 with a hollow fiber membrane 35, the feeding volume is within the hollow fiber lumen 36. When providing a plurality of hollow fiber membranes, the plurality of lumen 36 of the hollow fiber membranes provide the feeding volume 20.

The feeding volume 20 has a first feeding side opening 21 and a second feeding side opening 22. The hollow fiber membranes may be sealed to the filter housing so as to avoid bypassing of fluid without the fluid passing through the filter medium. The sealing may be realized by potting with epoxy resin, polyurethane, melting of filter housing polymer etc.

A first blood pump 110 may be coupled to the first feeding side opening 21, whereas a second blood pump 120 may be coupled to the second feeding side opening 22. The first feeding side opening 21 and the second feeding side opening 22 may be used to couple a respective blood pump to the filter housing 10. When providing one or a plurality of hollow fiber membranes 35, each of the hollow fiber lumen has a first end-side (terminal) opening 31 and a second end-side (terminal) opening 32. Each of the first end-side openings 31 of the lumen 36 may be coupled to the first feeding side opening 21 and each of the second end-side openings 32 of the lumen 36 may be coupled to the second feeding side opening 22. Thus, also a plurality of hollow fiber membranes may be coupled to the first and second feeding side openings 21, 22.

When starting the filtering process, a first blood pump 110 may feed the blood through the first feeding side opening 21 into the feeding volume 20. The filter membrane is adapted to allow the blood plasma/serum to pass and to retain the blood cells. Thus, the plasma/serum passes the wall of the filter membrane 30 and arrives at the clean side 40 of the filter, which clean side in the embodiment shown in FIG. 1 is within the filter housing 10. Thus, the blood plasma/serum 98 passes the filter membrane 30 and is collected in the clean side of the filter housing 10. The blood cells 99 will be retained on the raw side of the filter membrane 30 and sooner or later will exit the filter housing 10 through the second feeding side opening 22 and pass into a collecting container.

The collecting container may be, for example, a second blood pump 120, having a receiving volume. The receiving volume of the second blood pump may be, for example, a variable volume 121, which may expand when receiving the whole blood 97 with the blood cells 99 that has lost at least a part of the blood plasma/serum 98. The variable volume may be realized by a resilient material as illustrated in FIG. 1.

The variable volume may also be realized by a cylinder and piston, as illustrated in the alternative of FIG. 1. The elements to the left of the dashed line may be the same as described above. The piston may be spring loaded to generate an automatic return flow when lowering the pressure on the first pump side. The spring load may be provided by a mechanical spring or a compressible air volume.

As a particular length of the filter membrane or a hollow fiber membrane may allow only a small portion of the blood plasma/serum 98 to pass during one iteration, the collected blood 97 within the receiving volume of the second blood pump may flow back to repeat the filtering process. Thus, a plurality of forward and backward flow iterations may be conducted, wherein each of the flow-through passes may separate a certain part of the blood plasma/serum so that sooner or later the required amount of blood plasma/serum is collected in the filter housing 10 on the clean side 40 of the filtration device. The separated blood plasma/serum 98 may exit the filter housing 10 through the outlet opening 41 to be collected, for example, in a further plasma/serum container.

The hollow fiber membranes may be made of a ceramic material or of a polymeric material. The hollow fiber membrane 35 or in general the hollow fiber filter membrane may have a pore size allowing the blood plasma/serum to pass and retaining the blood cells. The pore size may be, for example, between 100 nanometers and 1,000 nanometers. The surface of the hollow fiber membrane 35 may be of a roughness lower than 10 microns in order to avoid the destruction of blood cells. The hollow fiber membrane 35 may be pre-flushed with an isotonic salt solution, in particular an isotonic NaCl solution. This pre-flushing humidifies the surface of the filter membrane and covers the filter membrane with sodium ions and chloride ions. The NaCl concentration in the isotonic solution is chosen so that the osmotic pressure is the same in the isotonic solution and in the blood cells so that an osmotic pressure difference may be avoided. Additionally, the pre-flushing fills the membrane pores with liquid and reduces capillary forces of the hydrophilic filter membrane material which are considered to be responsible for hemolysis due to blood contact with a porous filter material. Pre-flushing may be carried out by flowing an isotonic solution through the device before filtration of blood, for example, immediately before starting the blood filtration or a couple of minutes before blood filtration.

The hollow fiber membrane may be coated to modify the surface wettability of the filter membrane material. The capillarity can be reduced when the filter area at the lumen is made more hydrophobic and therefore hemolysis can be prevented.

Figure 2:
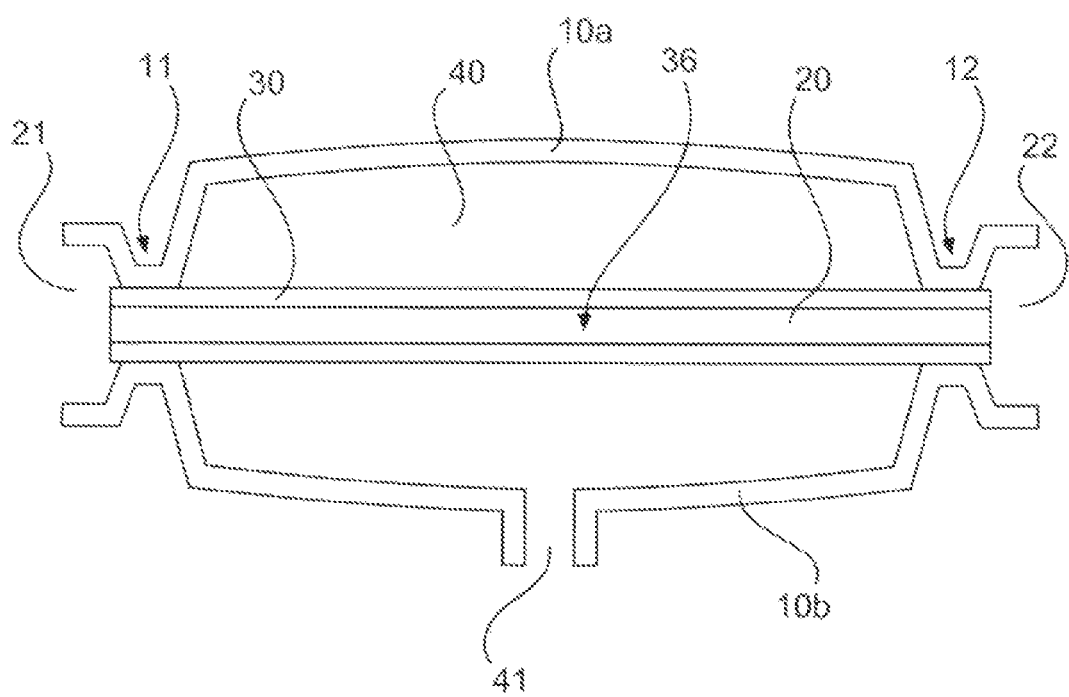
FIG. 2 illustrates an exemplary embodiment of a two-part filter housing.

FIG. 2 illustrates a further embodiment of a filter housing 10 having a first upper filter housing part 10a and a second or bottom filter housing part 10b. It should be noted that the filter housing 10 may be composed of more than two filter housing parts. The bottom filter housing part 10b in FIG. 2 comprises an outlet opening 41 for providing the filtered plasma/serum. A further container may be coupled to the outlet opening. This container may be adapted to be evacuated to generate an enlarged pressure difference between the feeding volume 20 and the clean side 40. The membrane 30, here in form of a hollow fiber membrane or a hollow fiber membrane bundle, may be tightly sealed between the both filter housing portions 10a, 10b. The clamping portions 11, 12 may correspond to the feeding openings 21, 22. This enables an easy manufacturing process.

Figure 3:
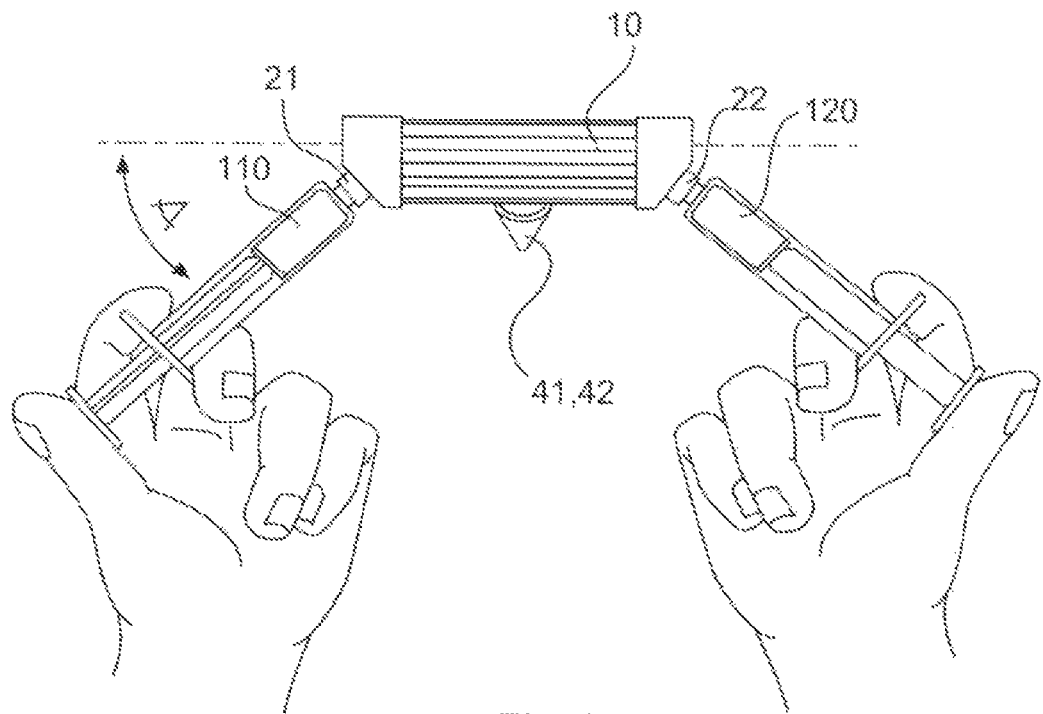
FIG. 3 illustrates an exemplary embodiment of the invention of a whole blood filtration device.

FIG. 3 illustrates an exemplary embodiment of the whole blood filtration device, which has a filter housing 10, a first blood pump 110, and a second blood pump 120. The filter housing has a first feeding side opening 21 and a second feeding side opening 22. The first feeding side opening 21 has a first opening orientation which is inclined with respect to the longitudinal extension of the filter housing 10. The second feeding side opening 22 has an opening orientation which is also inclined with respect to the longitudinal extension of the filter housing 10. The inclination is between 10° and 80°, preferably between 30° and 60°, and more preferably 45° plus/minus 5°. The device has an outlet opening 41 for letting out the plasma or serum. It should be noted that a plasma or serum container 42 may be connected to the outlet opening 41, which plasma or serum container 42 may collect the plasma/serum for further analysis. It should be noted that the analysis may also take place within the plasma container 42. It should be noted that the filter housing 10 may taper toward the outlet opening 41 so that the plasma or serum will automatically arrive at the outlet opening 41, provided the orientation of the filter housing is correct. The tapering and the outlet 41 are arranged opposed or normal to the orientation of the feeding side openings.

Figure 4:
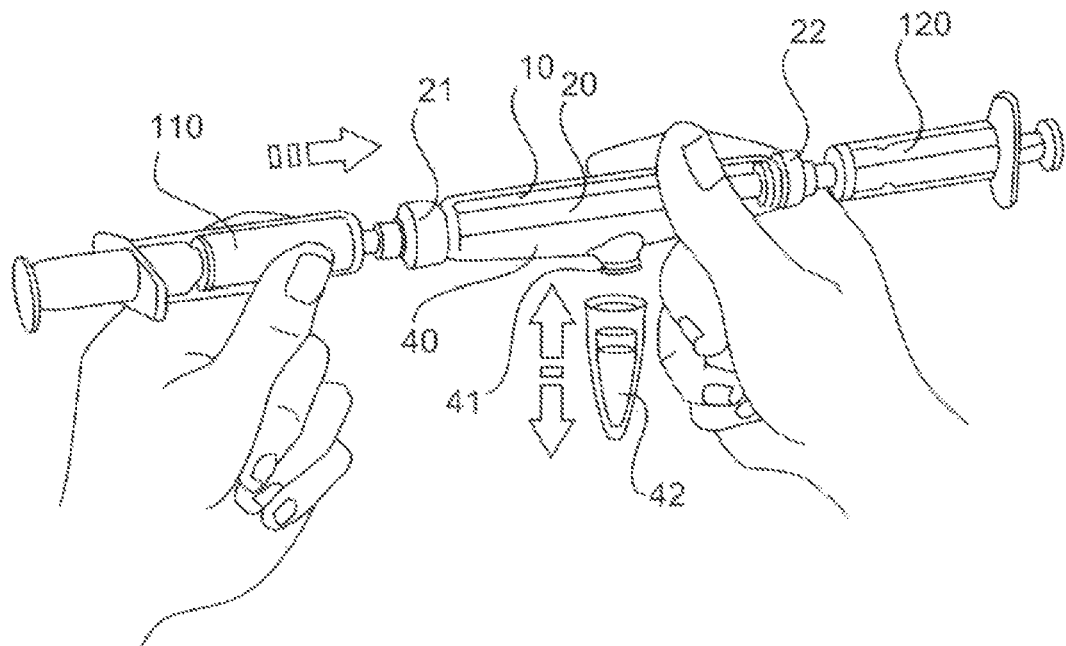
FIG. 4 illustrates an assembling of an exemplary whole blood filtration device.

FIG. 4 illustrates assembling of an exemplary embodiment of the whole blood filtration device having a filter housing 10 which is axially elongated, having an outer wall extending from a first axial end 21 of the filter housing to an opposite second axial end 22 of the filter housing. A first feeding side opening 21 is formed at the first axial end of the filter housing. A second feeding side opening 22 is formed at the opposite second axial end of the filter housing. The pump units 110 and 120 may be plugged into the feeding side openings 21, 22. The embodiment shown in FIG. 4 has substantially no inclination between the feeding orientation of the first feeding side opening and the second feeding side opening and the longitudinal extension of the filter housing 10. The blood sample contained, for example, in the first blood pump 110 may be pushed through the filter volume 20 so that the plasma or serum will pass through the filter medium to arrive at the clean side 40. The collected plasma or serum may exit the filter housing 10 through the outlet opening 41. As shown in FIG. 4, the plasma serum outlet opeing 41 is positioned midway between and spaced apart from both the first axial end 21 and the opposite second end 22 of the axially elongated filter housing 10. The collected plasma or serum may be collected in the plasma or serum container 42.

As shown in FIG. 4, the outer wall of the filter housing 10 has a taper which expands the outer wall radially outwardly as the outer wall progresses from the first axial end 21 to the plasma/serum outlet opening 41, and the filter housing 10 has a taper which expands the outer wall radially outwardly as the outer wall progresses from the opposite second axial end 22 to the plasma/serum outlet opening 41, the taper forming a slope urging the plasma/serum to flow in a direction to the plasma/serum outlet opening 41. It should be noted that the filter housing 10 (not only the filter housing of FIG. 4, but generally the filter housings of the invention) may have a hydrophobic surface or a hydrophobic coating so that no or less waste of plasma or serum occurs as a result of adhesion to the filter housing wall.

As described above, the filter housing 10 may be tapered toward the outlet opening 41 so that the plasma or serum will automatically arrive at the outlet opening 41, provided the orientation of the filter housing is correct.

Figure 5:
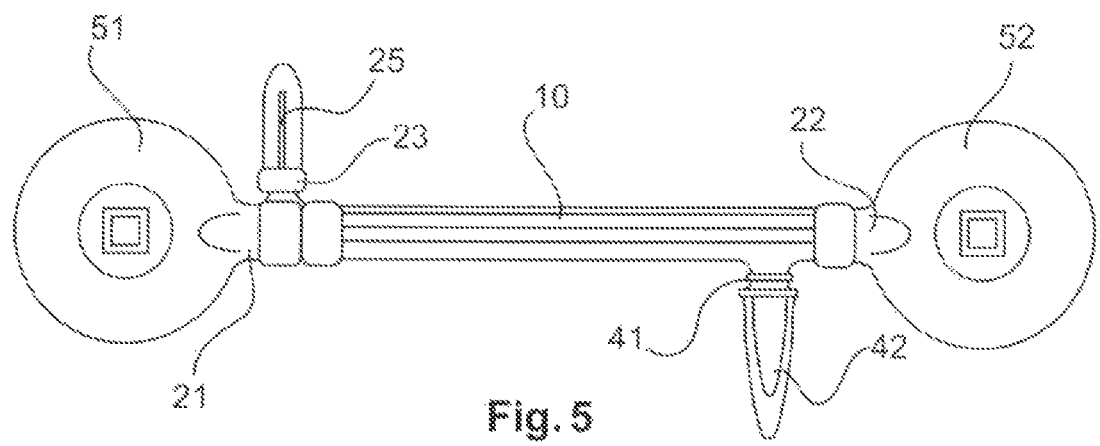
FIG. 5 illustrates an exemplary embodiment with balloon pumps.

FIG. 5 illustrates a further exemplary embodiment of the invention, wherein the blood pump is designed as a balloon 51, 52. The device illustrated in FIG. 5 further comprises a blood sample inlet 23 having, for example, a cannula needle 25 to receive an external blood container, which is not illustrated in FIG. 5. The balloons 51, 52 may be fixedly connected to the filter housing 10 at the feeding side openings 21, 22. Thus, the entire device may be kept hermetically closed so that the only openings are the inlet opening 23 and the outlet opening 41. A plasma or serum container 42 may be connected to the outlet opening 41.

Figure 6:
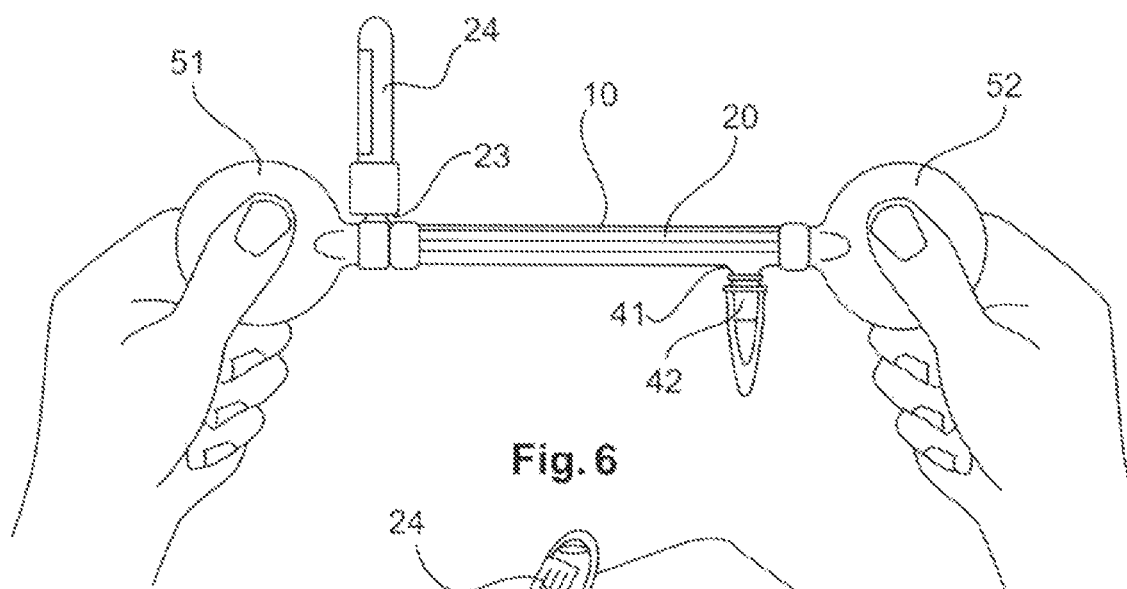
FIG. 6 illustrates handling of the exemplary embodiment with balloon pumps.

FIG. 6 illustrates handling of the device illustrated in FIG. 5. A blood container 24 will be plugged to the cannula needle 25, not illustrated in FIG. 6, to let the blood into the whole blood filtration device through the sample blood inlet 23. The blood will enter either the filter volume 20 or the balloon 51 so that, by alternately pushing the balloon 51 and 52, the blood may alternately flow through the filter volume 20 in order to gain the plasma or serum. The plasma/serum may exit the filter housing 10 through the outlet 41.

Figure 7:
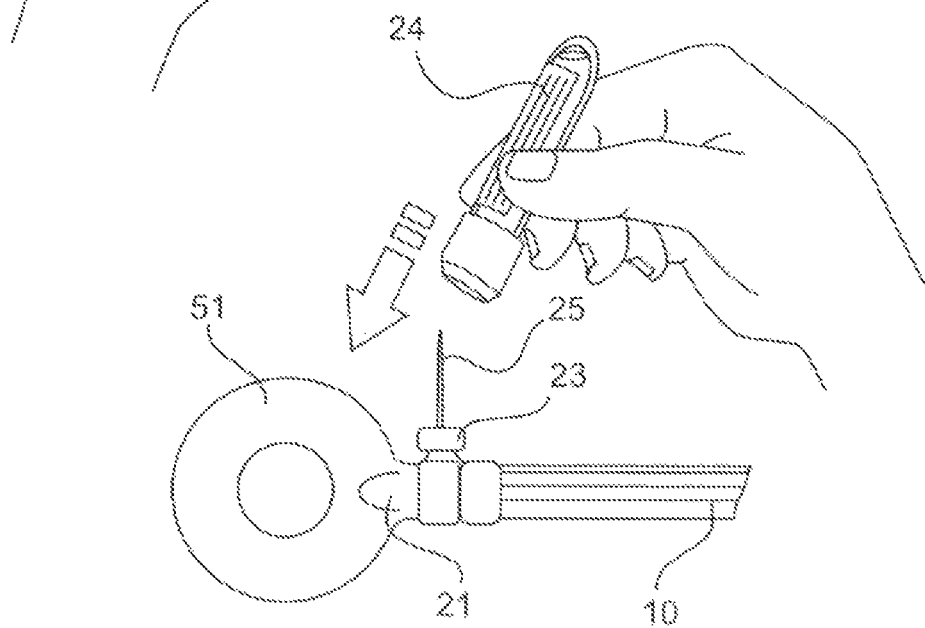
FIG. 7 illustrates plugging in a blood sample container according to an exemplary embodiment of the invention.

FIG. 7 illustrates the handling of the blood container 24, which will be plugged into the sample blood inlet opening 23. The blood container 24 may have a septum, which may be perforated by the cannula needle 25.

Figure 8:
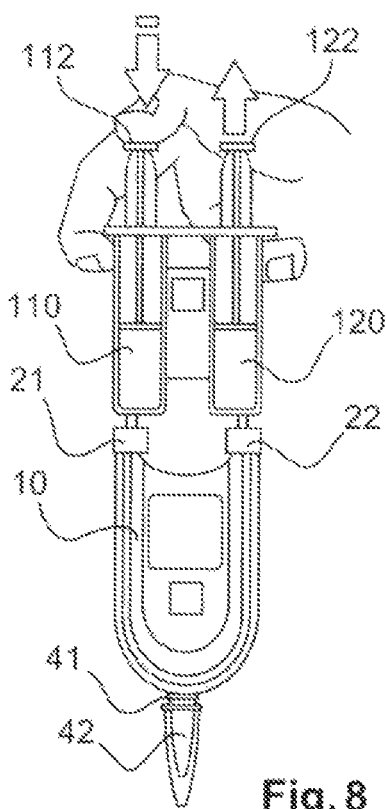
FIG. 8 illustrates a modular filtration device according to an exemplary embodiment of the invention.

FIG. 8 illustrates a further exemplary embodiment of the invention, wherein the filter housing 10 is U-shaped. The outlet opening 41 may be arranged at the bent portion of the U so that a plasma or serum container 42 may be connected thereto. The feeding side openings 21 and 22 have a corresponding opening orientation so that a blood pump 110 and a blood pump 120 may be arranged side by side. The first blood pump 110 and second blood pump 120 may be designed as a single unit so that coupling to the first and second inlet openings 21 and 22 may be conducted by a single step. The first blood pump 110 may have a first push button 112 and the second blood pump 120 may have a second push button 122. By arranging the both blood pumps 110, 120 side by side, having the same orientation of the push buttons 112, 122, the entire device may be easily operated as the operator may alternately push the both pump buttons 112, 122, as can be seen in FIG. 8.

Figure 9:
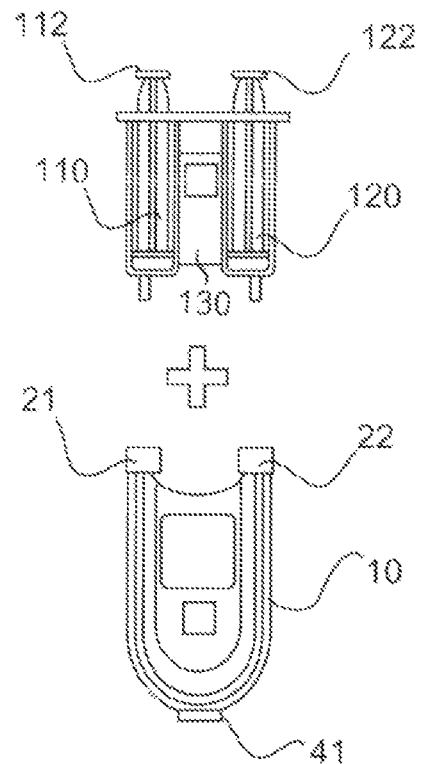
FIG. 9 illustrates the filter housing module and the pump module of the exemplary modular device.
Figure 10:
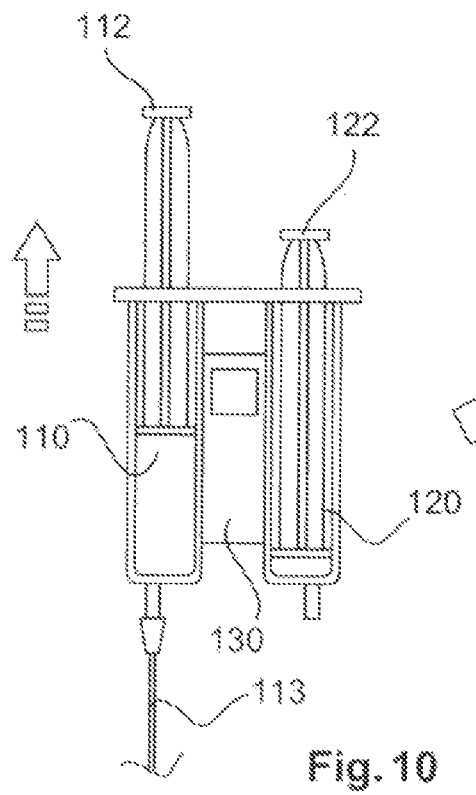
FIG. 10 illustrates a needle plugged into the pump unit.
Figure 11:
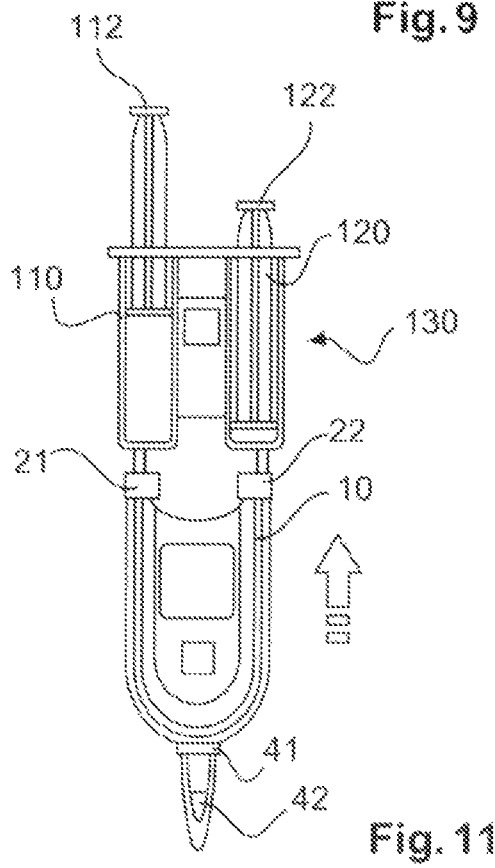
FIG. 11 illustrates a re-assembled modular filtration device according to an exemplary embodiment of the invention.

FIG. 9 illustrates the separated modules of the modular whole blood filtration device. One module is the filter housing 10 with the first and second feeding side openings 21 and 22, as well as the plasma or serum outlet opening 41. The other module is the pump module 130 which is formed by the first blood pump 110 and the second blood pump 120, each having a push button 112, 122. The separated pump unit 130 allows plugging in a needle 113, which can be seen in FIG. 10. Thus, it is possible to take blood from a patient by means of the needle 113 so that the blood can directly be transferred into the first blood pump 110 by pulling the push button 112. Afterwards, the needle will be removed, so that the pump unit 130 can be reassembled to the filter housing 10 so as to start the filtering process by alternately pushing the first and second push button 112, 122 until enough blood plasma is collected within the plasma container 42.

While specific embodiments of the invention have been shown and described in detail to illustrate the inventive principles, it will be understood that the invention may be embodied otherwise without departing from such principles.

LIST OF REFERENCE CHARACTERS 1 filtration device (filter)
10 filter housing
10a upper filter housing part
10b bottom filter housing part
11 first clamping portion
12 second clamping portion
20 feeding volume
21 first feeding side opening
22 second feeding side opening
23 sample inlet opening
24 sample blood container
25 cannula needle at sample inlet opening
30 filter membrane
31 first end-side opening of lumen
32 second end-side opening of lumen
35 hollow fiber membrane
36 lumen of hollow fiber membrane
40 clean side
41 outlet opening
42 plasma/serum container
51 first balloon pump
52 second balloon pump
97 blood/whole blood
98 blood plasma/serum
99 blood cells
110 first blood pump
112 first pump bush button
113 cannula needle
120 second blood pump
121 resilient volume of second blood pump
122 second pump push button
130 pump unit

What is claimed is:

1. A whole blood filtration device separating blood plasma/serum from blood cells and collecting the separated plasma/serum in a connection container for analysis, the whole blood filtration device comprising:
a filter housing which is axially elongated, having an outer wall extending from a first axial end of the filter housing to an opposite second axial end of the filter housing, the filter housing, comprising:
a first feeding side opening at the first axial end of the filter housing;
a second feeding side opening at the opposite second axial end of the filter housing;
two blood pumps, wherein one or both blood pumps is a manual blood pump, the two blood pumps comprising:
a first blood pump of the two blood pumps coupled onto the first feeding side opening; and
a second blood pump of the two blood pumps coupled onto the second feeding side opening;
a filter membrane separating a feeding volume and a clean side of the filter membrane from each other, the filter membrane arranged in an interior of the filter housing, wherein the filter membrane comprises at least one hollow fiber membrane comprising a lumen including a first terminal opening and a second terminal opening;
wherein the lumen in an interior of the at least one hollow fiber membrane forms the feeding volume, the first feeding side opening in communication with the first terminal opening and the second feeding side opening is in communication with the second terminal opening, the feeding volume communicating with a first feeding side opening and with a second feeding side opening, the first feeding side opening is coupled to the first blood pump for feeding blood from the first feeding side opening into the feeding volume so that blood plasma/serum permeates the filter membrane and blood cells, retained by the filter membrane, exit from the feeding volume through the second feeding side opening, wherein the second feeding side opening is coupled to the second blood pump for releasing blood from the second feeding side opening into the feeding volume so that a blood plasma/serum permeates the filter membrane and blood cells, retained by the filter membrane, exit from the feeding volume through the first feeding side opening;

wherein the at least one hollow fiber membrane comprises a hydrophilicity-reducing coating, wherein the term "hydrophilicity-reducing" is defined to refer to a water or blood droplet contact angle of the at least one hollow fiber membrane which is larger than a water or blood droplet contact angle of the at least one hollow fiber membrane prior to coating;

the filter membrane including pores with a pore size that ensures permeability of the filter membrane to blood plasma/serum and that retains blood cells, the pore size is between 100 nanometers and 1,000 nanometers, the filter membrane having a roughness lower than 10 microns;

wherein the interior of the filter housing at the clean side is hydrophobically coated, wherein the filter housing further comprises:
a plasma/serum outlet opening formed in the outer wall of the filter housing and positioned midway between and spaced apart from both the first axial end and the opposite second end of the filter housing, the plasma/serum outlet opening in communication with the clean side of the at least one hollow fiber membrane;
wherein the outer wall of the filter housing has a taper which expands the outer wall radially outwardly as the outer wall progresses from the first axial end to the plasma/serum outlet opening, and the filter housing has the taper which expands the outer wall radially outwardly as the outer wall progresses from the opposite second axial end to the plasma/serum outlet opening, the taper forming a slope urging the plasma/serum to flow in a direction to the plasma/serum outlet opening.

2. The whole blood filtration device according to claim 1, wherein
the at least one hollow fiber membrane is a membrane pre-treated by pre-flushing with an ionic solution.

3. The whole blood filtration device according to claim 2, wherein
the ionic solution is a NaCl solution.

4. The whole blood filtration device according to claim 1, wherein
the hydrophilicity-reducing coating is a hydrophobic coating.

5. The whole blood filtration device according to claim 1, wherein
the material of the at least one hollow fiber membrane is a ceramic material comprising the pores with the pore size that ensures permeability of the filter membrane to blood plasma/serum and that retains blood cells.

6. The whole blood filtration device according to claim 1, wherein
the first blood pump is a manual blood pump and when de-coupled from the filter housing is configured to be removably coupled to a cannula needle to take blood from a patient.

7. The whole blood filtration device according to claim 6, wherein the second blood pump comprises a resilient volume configured to be subjected to a biasing force when receiving a blood fluid and configured to release the blood fluid when the biasing force is reduced.

8. The whole blood filtration device according to claim 7, wherein the second blood pump is a resilient rubber or a spring-loaded plunger.

9. The whole blood filtration device according to claim 1, wherein both blood pumps are piston-driven manual blood pumps, each having a push button actuator having a corresponding push button actuator orientation, wherein the push button actuators are arranged for alternate manual operation when the whole blood filtration device is handheld.

10. The whole blood filtration device according to claim 1, wherein
the first feeding side opening has a first opening orientation and the second feeding side opening has a second opening orientation,
wherein the first opening orientation is inclined at a first inclination relative to the longitudinal extension of the filter housing and the second opening orientation is inclined at a second inclination relative to the longitudinal extension of the filter housing,
wherein the first and second inclinations each are between 10° and 80°.

11. The whole blood filtration device according to claim 10, wherein the first and second inclinations are between 30° and 60°.

12. The whole blood filtration device according to claim 11, wherein the first and second inclinations are 45°+/−5°.

* * * * *